United States Patent
Law et al.

(10) Patent No.: US 10,413,692 B2
(45) Date of Patent: Sep. 17, 2019

(54) CUSHION ASSEMBLY

(71) Applicant: ResMed Limited, Bella Vista (AU)

(72) Inventors: Kam Man Law, Sydney (AU);
Matthew Robin Wells, Manly (AU)

(73) Assignee: ResMed Pty Ltd (AU)

( * ) Notice: Subject to any disclaimer, the term of this patent is extended or adjusted under 35 U.S.C. 154(b) by 275 days.

(21) Appl. No.: 14/172,149

(22) Filed: Feb. 4, 2014

(65) Prior Publication Data

US 2014/0216462 A1    Aug. 7, 2014

(30) Foreign Application Priority Data

Feb. 4, 2013    (AU) .................. 2013900349

(51) Int. Cl.
*A61M 16/06*    (2006.01)
(52) U.S. Cl.
CPC ..... *A61M 16/0616* (2014.02); *A61M 16/0683* (2013.01)
(58) Field of Classification Search
CPC .......... A61M 16/0616; A61M 16/0683; A61M 16/06
USPC ..................................... 128/205.25
See application file for complete search history.

(56) References Cited

U.S. PATENT DOCUMENTS

| | | | |
|---|---|---|---|
| 4,323,063 A | 4/1982 | Fisichella | |
| 4,782,832 A | 11/1988 | Trimble et al. | |
| 4,803,981 A | 2/1989 | Vickery | |
| 4,944,310 A | 7/1990 | Sullivan | |
| 4,945,907 A | 8/1990 | Tayebi | |
| 5,429,683 A | 7/1995 | Le Mitouard | |
| 5,662,101 A | 9/1997 | Ogden | |
| 6,196,223 B1 | 3/2001 | Belfer et al. | |
| 6,532,959 B1 | 3/2003 | Berthon-Jones | |
| 6,581,594 B1 | 6/2003 | Drew et al. | |
| 7,152,602 B2 | 12/2006 | Bateman et al. | |
| 7,448,386 B2 | 11/2008 | Ho et al. | |
| D582,546 S | 12/2008 | Fujiura et al. | |
| 7,472,703 B2 | 1/2009 | Hernandez et al. | |
| 7,546,837 B2 | 6/2009 | Busch | |
| 7,575,006 B2 | 8/2009 | Schegerin | |
| 7,708,017 B2 | 5/2010 | Davidson et al. | |

(Continued)

FOREIGN PATENT DOCUMENTS

| | | | |
|---|---|---|---|
| EP | 0288937 A2 | 11/1988 | |
| EP | 0288938 A2 | 11/1988 | |

(Continued)

OTHER PUBLICATIONS

International Search Report & Written Opinion for Application No. PCT/AU2014/000077 dated Apr. 23, 2014.

(Continued)

*Primary Examiner* — Tan-Uyen T Ho
*Assistant Examiner* — Margaret M Luarca
(74) *Attorney, Agent, or Firm* — Botos Churchill IP Law LLP

(57) ABSTRACT

A foam cushion assembly for a patient interface, the foam cushion assembly being adapted to couple with a patient interface frame, the cushion assembly comprising a substantially above the nose seal portion and a mouth seal portion, wherein the cushion assembly comprises a foam cushion arranged to form with the frame a common plenum chamber for sealing about the nose and mouth.

63 Claims, 18 Drawing Sheets

(56) References Cited

U.S. PATENT DOCUMENTS

| | | |
|---|---|---|
| 8,028,699 B2 | 10/2011 | Ho et al. |
| 8,220,459 B2 | 7/2012 | Davidson et al. |
| 8,347,886 B2 | 1/2013 | Ho et al. |
| D693,460 S | 11/2013 | Rothermel et al. |
| D693,462 S | 11/2013 | Rothermel et al. |
| 8,701,667 B1 | 4/2014 | Ho et al. |
| 8,869,797 B2 | 10/2014 | Davidson et al. |
| D751,188 S | 3/2016 | Skipper et al. |
| D769,440 S | 10/2016 | Amarasinghe et al. |
| 2002/0029780 A1* | 3/2002 | Frater .................. A61M 16/06 128/206.24 |
| 2003/0168063 A1 | 9/2003 | Gambone et al. |
| 2005/0199242 A1 | 9/2005 | Matula et al. |
| 2005/0257792 A1 | 11/2005 | Wixey et al. |
| 2006/0118117 A1 | 6/2006 | Berthon-Jones et al. |
| 2007/0006879 A1 | 1/2007 | Thornton |
| 2007/0044804 A1 | 3/2007 | Matula, Jr. |
| 2007/0125385 A1 | 6/2007 | Ho et al. |
| 2007/0125386 A1* | 6/2007 | Quinn .............. A61M 16/0683 128/207.11 |
| 2007/0145534 A1 | 6/2007 | Murakami |
| 2007/0215161 A1* | 9/2007 | Frater .................. A61M 16/06 128/206.24 |
| 2008/0257354 A1 | 10/2008 | Davidson et al. |
| 2009/0014007 A1 | 1/2009 | Brambilla et al. |
| 2009/0044808 A1 | 2/2009 | Guney et al. |
| 2009/0050156 A1 | 2/2009 | Ng et al. |
| 2009/0139525 A1 | 6/2009 | Schirm |
| 2009/0255542 A1 | 10/2009 | Ugai et al. |
| 2010/0000534 A1 | 1/2010 | Kooij et al. |
| 2010/0028425 A1 | 2/2010 | Mehta et al. |
| 2010/0108072 A1 | 5/2010 | D'Souza et al. |
| 2010/0319700 A1 | 12/2010 | Ng et al. |
| 2010/0326445 A1 | 12/2010 | Veliss |
| 2011/0005524 A1 | 1/2011 | Veliss et al. |
| 2011/0088698 A1 | 4/2011 | Barnett et al. |
| 2011/0146684 A1* | 6/2011 | Wells ................ A61M 16/06 128/205.25 |
| 2011/0209701 A1 | 9/2011 | Derringer et al. |
| 2012/0080035 A1 | 4/2012 | Guney et al. |
| 2012/0090617 A1 | 4/2012 | Matula, Jr. |
| 2012/0204879 A1* | 8/2012 | Cariola .............. A61M 16/06 128/206.24 |
| 2012/0204881 A1 | 8/2012 | Davidson et al. |
| 2012/0222680 A1* | 9/2012 | Eves ............... A61M 16/0683 128/206.24 |
| 2013/0104902 A1 | 5/2013 | Ho et al. |
| 2013/0133664 A1 | 5/2013 | Startare |
| 2013/0199537 A1 | 8/2013 | Formica et al. |
| 2013/0306077 A1 | 11/2013 | Greenberg |
| 2014/0216462 A1 | 8/2014 | Law et al. |
| 2014/0224253 A1 | 8/2014 | Law |
| 2014/0261435 A1 | 9/2014 | Rothermel |
| 2014/0290663 A1 | 10/2014 | Rothermel |
| 2014/0311496 A1 | 10/2014 | Rothermel |
| 2015/0000671 A1 | 1/2015 | Frerichs et al. |
| 2015/0328423 A1 | 11/2015 | Siew et al. |
| 2016/0325067 A1 | 11/2016 | Harwood et al. |

FOREIGN PATENT DOCUMENTS

| | | |
|---|---|---|
| EP | 0427474 A2 | 5/1991 |
| EP | 2213324 A1 | 8/2010 |
| EP | 2428241 A1 | 3/2012 |
| GB | 2385533 A | 8/2003 |
| TW | M253360 U | 12/2004 |
| TW | I357340 B | 2/2012 |
| WO | 97/09090 A1 | 3/1997 |
| WO | 19980004310 A1 | 2/1998 |
| WO | 19980034665 A1 | 8/1998 |
| WO | 9925410 A1 | 5/1999 |
| WO | 20000078381 A1 | 12/2000 |
| WO | 0195965 A1 | 12/2001 |
| WO | 2004007010 A1 | 1/2004 |
| WO | 2004041342 A1 | 5/2004 |
| WO | 2004073778 A1 | 9/2004 |
| WO | 2005063328 A1 | 7/2005 |
| WO | 20060074513 A1 | 7/2006 |
| WO | 2006130903 A1 | 12/2006 |
| WO | 2007009182 A1 | 1/2007 |
| WO | 2007133332 A2 | 11/2007 |
| WO | 2008011682 A1 | 1/2008 |
| WO | 2008011683 A1 | 1/2008 |
| WO | 2008070929 A1 | 6/2008 |
| WO | 2009052560 A1 | 4/2009 |
| WO | 2009108994 A1 | 9/2009 |
| WO | 2009109004 A1 | 9/2009 |
| WO | 2010028425 A1 | 3/2010 |
| WO | 2010148453 A1 | 12/2010 |
| WO | 20100135785 A1 | 12/2010 |
| WO | 2011060479 A1 | 5/2011 |
| WO | 2012177152 A1 | 12/2012 |
| WO | 2016054692 A2 | 4/2016 |

OTHER PUBLICATIONS

Taiwan Search Report for Taiwanese Application No. 103103848 dated Jan. 11, 2017.

Supplementary European Search Report for Application No. EP14746612 dated Sep. 26, 2016.

Japanese Patent Application No. 2015-555500 Office Action dated Dec. 8, 2017.

U.S. Non-Final Office Action issued in corresponding U.S. Appl. No. 14/765,492 dated May 2, 2018.

* cited by examiner

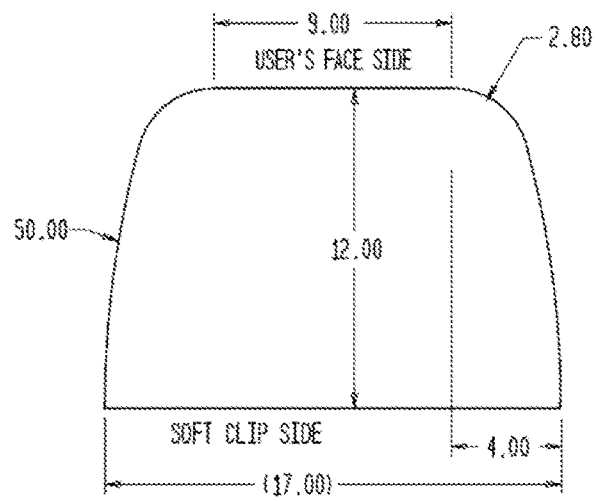
FIG. 10
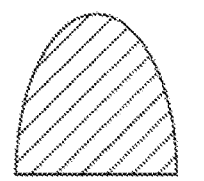
Rounded top
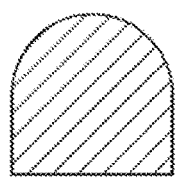
Rounded top – with straight sides
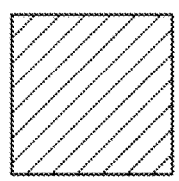
Rectangular
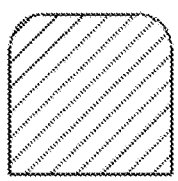
Rectangular with rounded edges
FIG. 11

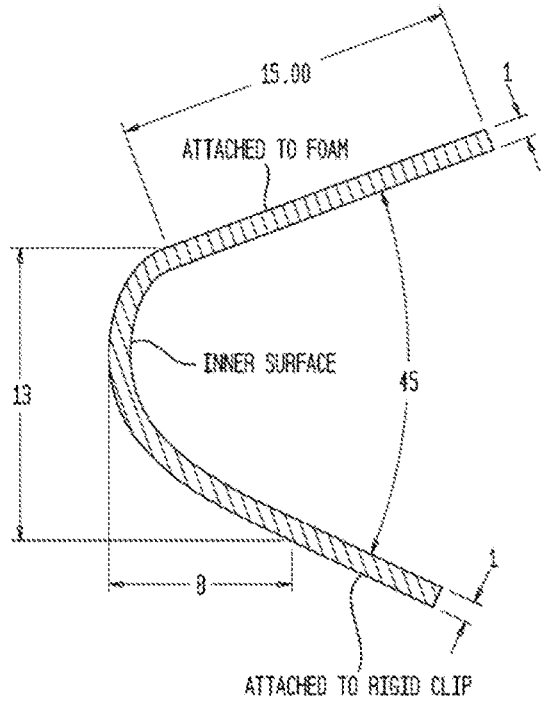
FIG. 16  (Cross section of the nasal bridge region)
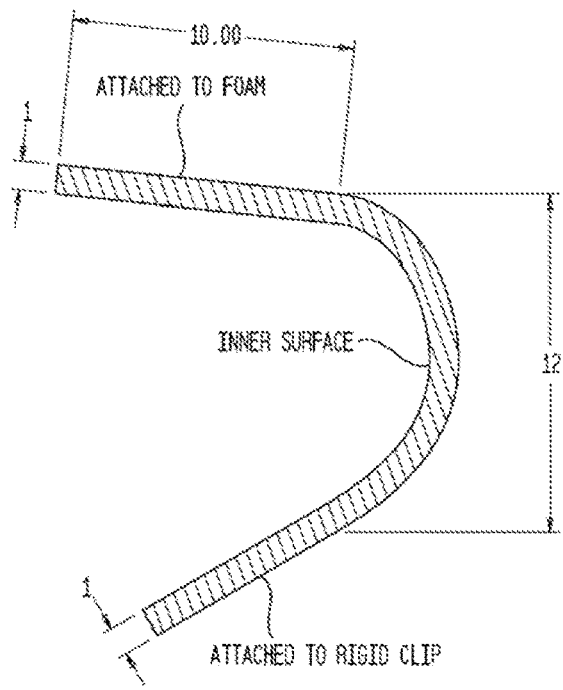
FIG. 17  (Cross section of side of nose region)

(Cross section of sides of mouth region)

(Cross section of bottom of mouth region)

CUSHION ASSEMBLY

CROSS-REFERENCE TO RELATED APPLICATIONS

The present application claims priority from Australian Provisional Patent No. 2013900349 filed Feb. 4, 2013, the disclosure of which is hereby incorporated herein by reference.

BACKGROUND OF THE INVENTION

Field of the Technology

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders. Such devices may include an interface for directing a treatment to a patient respiratory system.

Description of the Related Art and of the Problem to be Solved

Traditional Full Face mask (also referred to as a patient interface) obtains a seal with the user's face by way of a silicone cushion that seals both over the mouth and over the bridge of the nose. The main issue with this is that, due to the nature of the silicon material, often comfort issues are experienced by the user (i.e. facial markings, sores, allergic reaction).

This problem seems to be overcome by the use of foam. The compliant nature of foam allows it to, under relatively small tension force, compress into intricate facial features and affect a good seal. This, combined with the easy adaptability and softness experienced by the patient, provides for a relative fast and easy mask set-up. The foam also exhibits better breathability than silicone. Thus, the use of foam is associated with better cooling and reduced discomfort in the areas of contact in the sealing areas.

In order to achieve comfortable fit, a good seal and stability, current Full Face Foam masks are larger in footprint when compared to masks with traditional silicone seals.

To obtain the correct flow characteristics the foam being currently used is either not permeable or has a secondary layer over the foam to stop air from passing through the foam. Both options remove the breathability benefit of a foam seal. It should be noted that only foam full face masks having sealed or non-permeable foam cushions are compatible with current OSA respiratory therapy.

Some prior foam masks also involve separate individual components that together form the cushion. In one example, a foam layer may be attached to a silicon cushion to improve the sealing quality and the comfort associated with the mask. Such arrangements, apart from being large in size and less comfortable, also make it more difficult for the user to disassemble, assemble and clean the mask.

Some related prior art documents include: WO2007133332; WO2008070929; WO2009109004; WO2009108994; WO2010028425; WO2004041342; US 2008 0257354; WO2010148453; US_2012_0204879_A1; EP2213324 A1.

BRIEF SUMMARY OF THE INVENTION

A foam cushion assembly is designed to seal around the mouth and over the nasal bridge, which achieves a comfortable and effective seal, as shown in FIGS. 1 and 2. The assembly comprises a foam cushion portion, a soft clip portion and a rigid clip portion. The soft clip is arranged to complement the compliance of the cushion so as to allow a reduction in the size of the cushion.

In terms of comfort, the force applied to the user's face from the headgear and the treatment pressure from the seal interface is distributed over a larger surface area compared to traditional silicone based seals, resulting in better comfort.

Any leak is dispersed over a wider area resulting in a more dispersed flow, which minimise "jetting" of conventional silicone cushions.

Some key benefits include:

A breathable foam cushion assembly is designed which cools and reduces discomfort in sealing areas.

The footprint of the mask is reduced with the inclusion of the soft clip.

A soft clip allows a reduced overall dimension in the foam component of the cushion which increases stability without a compromise in comfort and sealing.

A foam cushion assembly that is relatively small in size, unobtrusive, yet easily removable for cleaning and replacement.

BRIEF DESCRIPTION OF DRAWINGS

FIGS. 8, 9 and 10 are cross sectional views of portions of a foam cushion in a nasal bridge region, a side of nose region and side of mouth region.

FIG. 11 illustrates several example cross sectional geometries for a foam cushion.

FIGS. 16, 17, 18 and 19 illustrate various cross sectional geometries for various regions of the clip component of FIG. 49.

DETAILED DESCRIPTION

Figure 1:
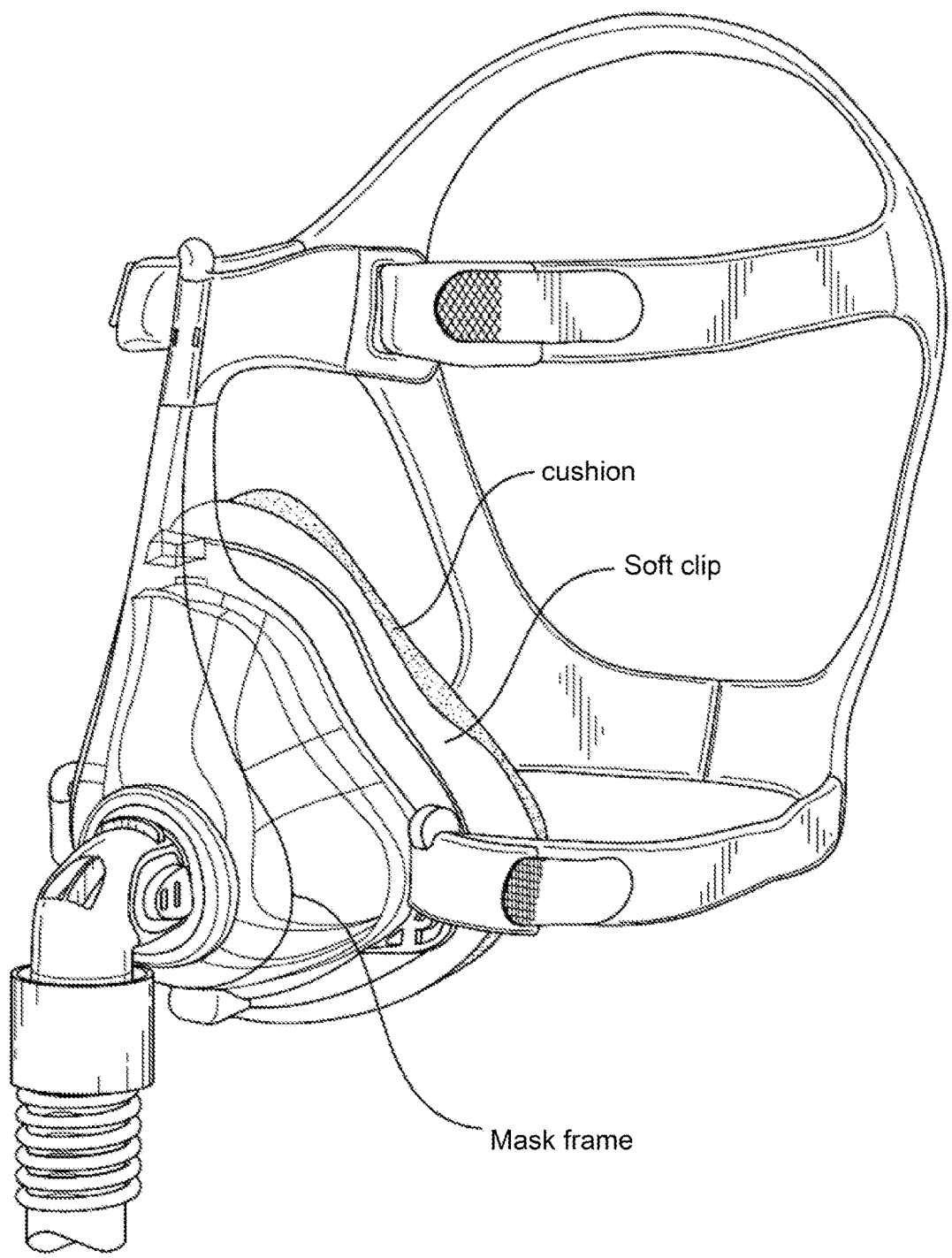
FIGS. 1 and 2 illustrate a foam mask, with headgear, configured for sealing with the mouth and over the nasal bridge.
Figure 2:
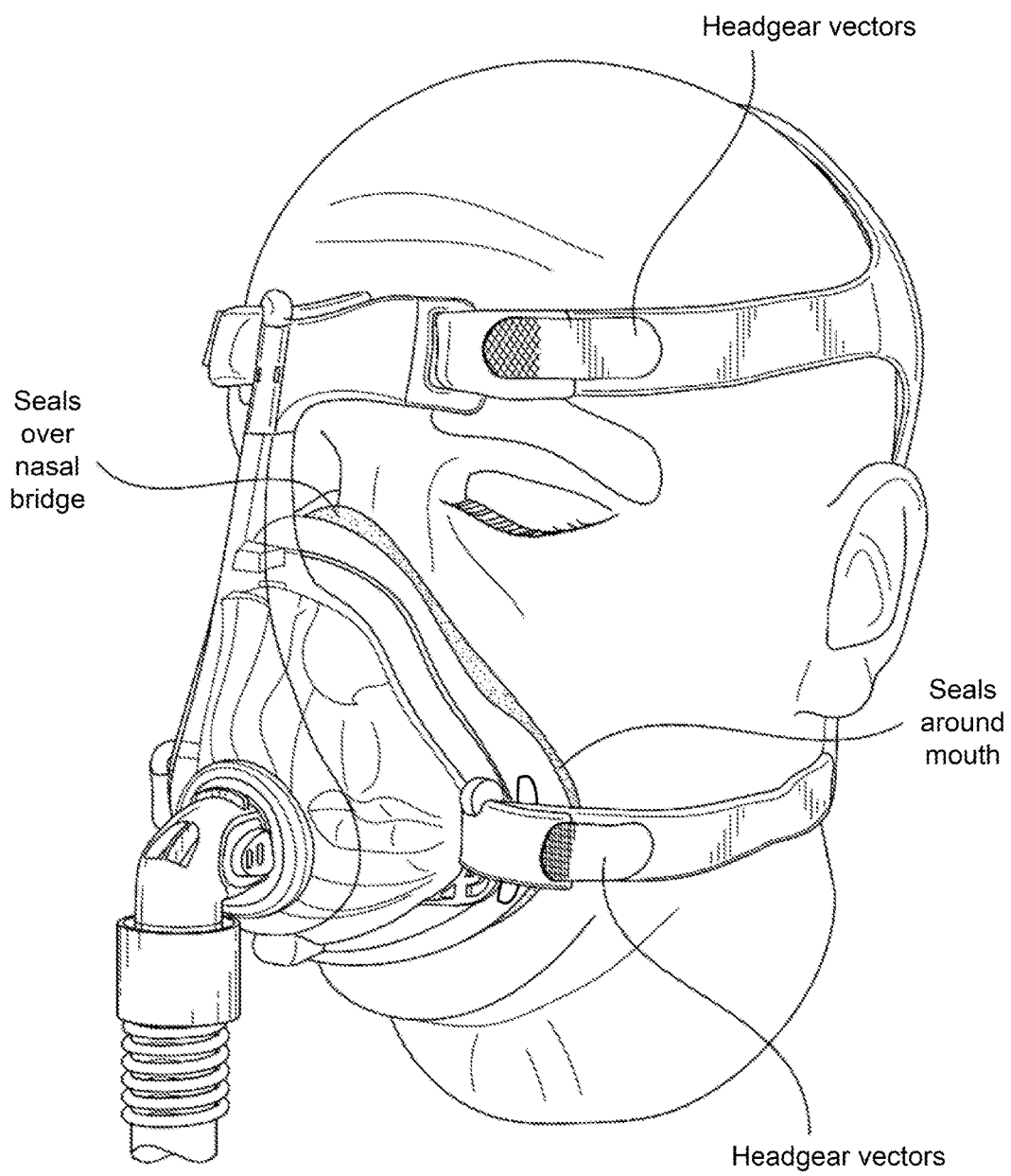
Figure 3:
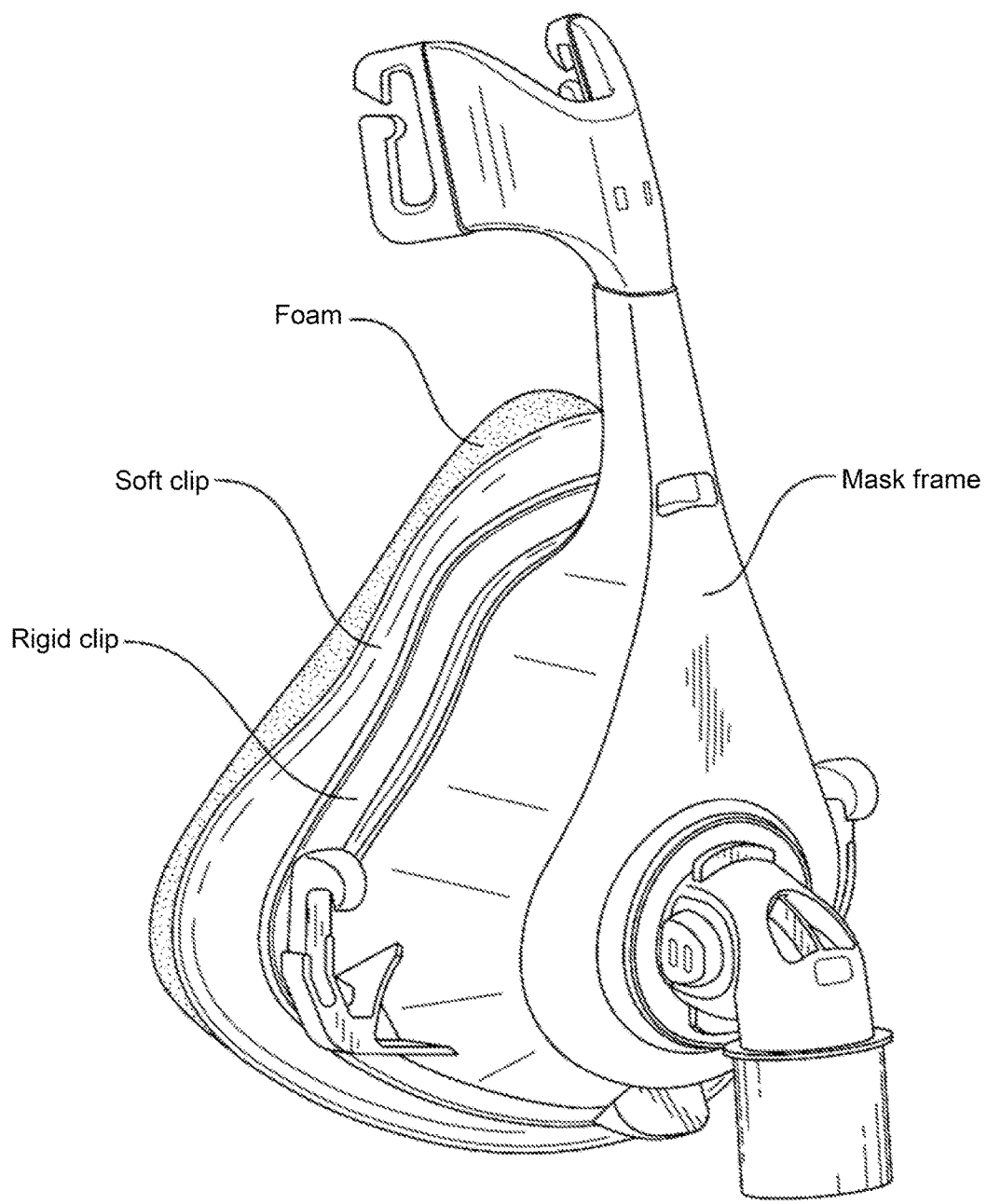
FIG. 3 is another view of the foam mask of FIG. 1 without the headgear.

In one embodiment, the cushion defines a single chamber that covers the patient's mouth and nose (approximately midway up the nasal bridge). The cushion has a substantially triangular or pear-like shape with a sealing face that follows the contours of a user's face. The single chamber foam cushion is designed to be attached to a first (soft) clip that that is itself attached to a second, more-rigid, clip (as shown in FIG. 3) or directly to the mask frame. In one embodiment, the first cushion clip is a flexible clip that is more rigid than the foam, but softer than the second clip. It is the combination of the foam and a soft and flexible clip that defines the physical properties of the overall sealing interface. The soft clip allows the interface to accommodate major variations, and to successfully conform to the contours of the patients face. The compliant nature of the foam cushion provides micro-adjustment and forms a comfort interface layer that interacts with the patient's skin. Whilst abandoning the clips and using a foam-only cushion assembly is possible, it may require the cushion to be of a substantial thickness and height. The use of a clip, even a rigid one, and especially of a combination of soft and rigid clips as described here, allows reduction in the dimensions of the foam cushion, without compromising on compliance, sealing and comfort. An assembled view of the cushion assembly is shown in FIG. 5.

Figure 5:
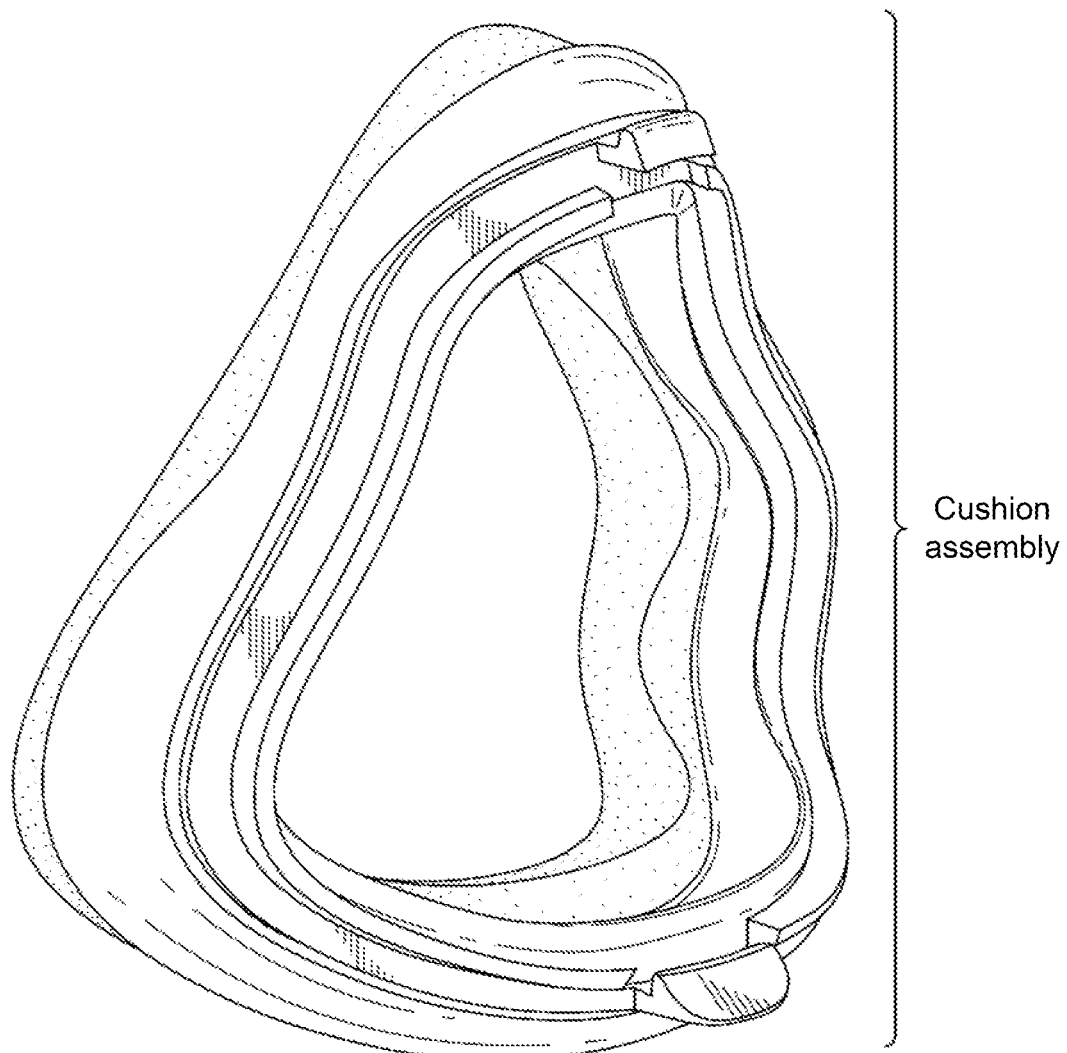
FIG. 5 shows the foam cushion assembly with the coupled components of FIG. 4.

In one embodiment the foam, soft clip and rigid clip are formed together or permanently attached, as shown in FIG. 5, forming an integral cushion assembly. The foam and soft clip form the compliant portion of the assembly, while the rigid clip provides the mechanism which attaches the cushion assembly to the mask frame. This allows the cushion assembly to be removed for cleaning and replacement. A rigid clip is used to enable a rigid connection between the cushion assembly the mask frame which makes it more convenient for handling and more durable.

Figure 4:
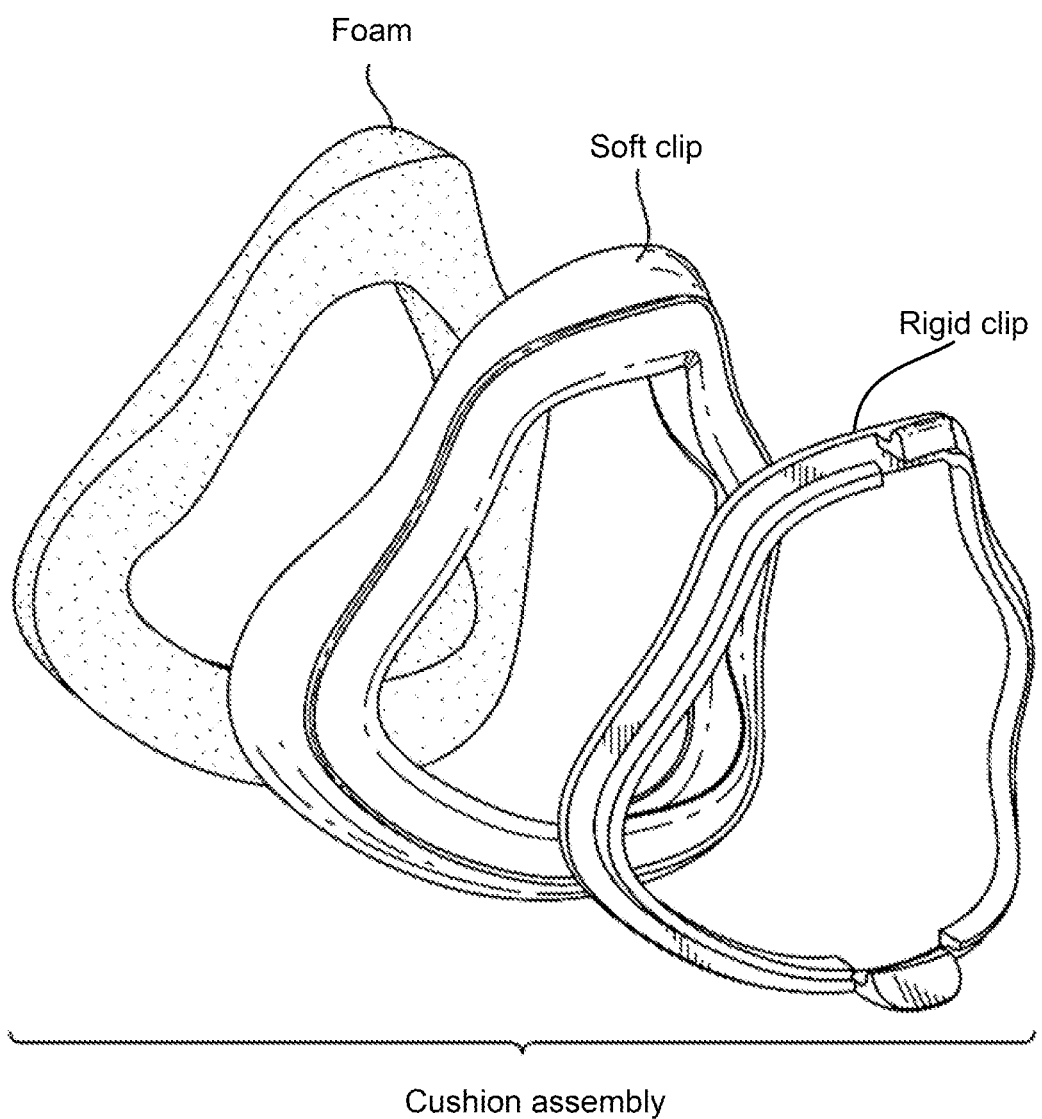
FIG. 4 is an illustration of separated components of a foam cushion assembly such as for the foam mask of FIG. 3.

It should be noted the components of the cushion assembly—the foam cushion, the soft clip and the more rigid clip can be permanently attached in one integral assembly. However, this does not have to be the case and they can represent separate elements, as shown in FIG. 4. These elements may be arranged to be assembled together, but dissembled and assembled again, if necessary. For example, the foam cushion and the soft clip can be permanently attached to each other, but detachably connected to the rigid clip. Alternatively, the soft clip and the more rigid clip can be permanently attached to each other but detachably connected to the foam cushion.

The mechanisms of such removable attachment are well known in the art and may include adhesive layers (for attaching the foam to the soft clip), interference fits and snap-locking engagements. The periphery of the more flexible components, such as the flexible clip, can also be stretched over the periphery of the more rigid component, such as the frame or the rigid clip.

Any combination of the three components is possible and alternative design variants could include a cushion assembly comprising only a foam cushion; a foam cushion and a soft clip or a foam cushion and a hard clip.

Sealing Mechanism

The seal around the mouth, the sides of the nose and the nasal bridge is produced through the interaction between the patient's face and the combined reaction of the frame (which is applied to the cushion assembly by way of the hard clip); the soft clip and the foam cushion, to the headgear tension. Details of these three components are discussed below. These components when assembled together work in unison to provide variable amounts of foam compression around the nose and mouth so that an effective seal is produced in these areas. The following sketch illustrates the mechanism that is created to, through the combination of these three components, achieve seal.

Figure 6:
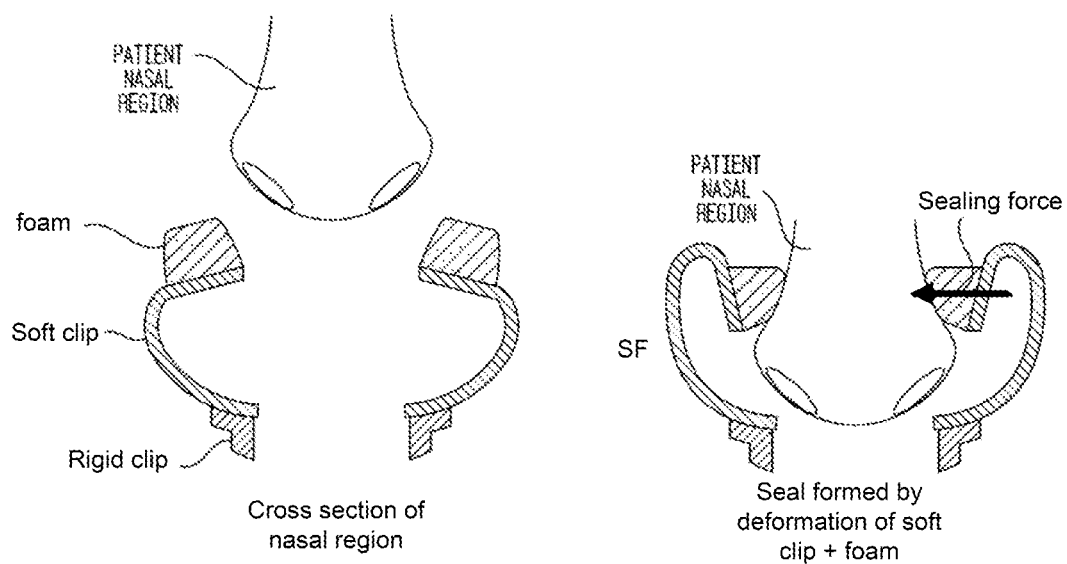
FIG. 6 illustrates mask sealing with a foam cushion in a nasal region with the mask of FIG. 4.

The sealing mechanism can be summarized through the following statements (refer to the illustration FIG. 6):

By applying the foam cushion onto the user's face and tightening the headgear vectors a seal is generated along the foam's contact surface with the patient's face, such as over the nasal bridge and around the sides of the nose and mouth. The seal is caused by a combination of foam compression and/or deflection and compression of the soft clip.

The flexibility in the combination of foam and soft clip will enable the foam to conform well to the patient's facial profile.

As the headgear vectors are further tightened, a greater sealing force will be applied.

The reaction forces in the cushion and the soft clip, caused by the deflection and compression of the cushion and clip, result in a reaction vector that is directed perpendicularly from the frame support and towards the patient.

The CPAP pressure accumulated inside the mask chamber also acts upon the soft clip and the foam, pushing them outwardly and compressing the foam against the user's face. Thus, the arrangement utilizes further the pressure in the chamber and helps maintaining sealing pressure. As mentioned above, because of their flexible nature, the foam and clip work in unison to respond to the compression force imparted to the frame by the headgear vectors. Eventually, when the requisite headgear tension has been applied and the frame is pulled towards the patient's face, the foam and clip will reach an equilibrium shape, in which a seal is created and retained. Once this has been achieved, the clip will provide the majority of the reaction force through its greater stiffness and elasticity.

The compressed foam may provide very little elastic reaction force.

Figure 7:
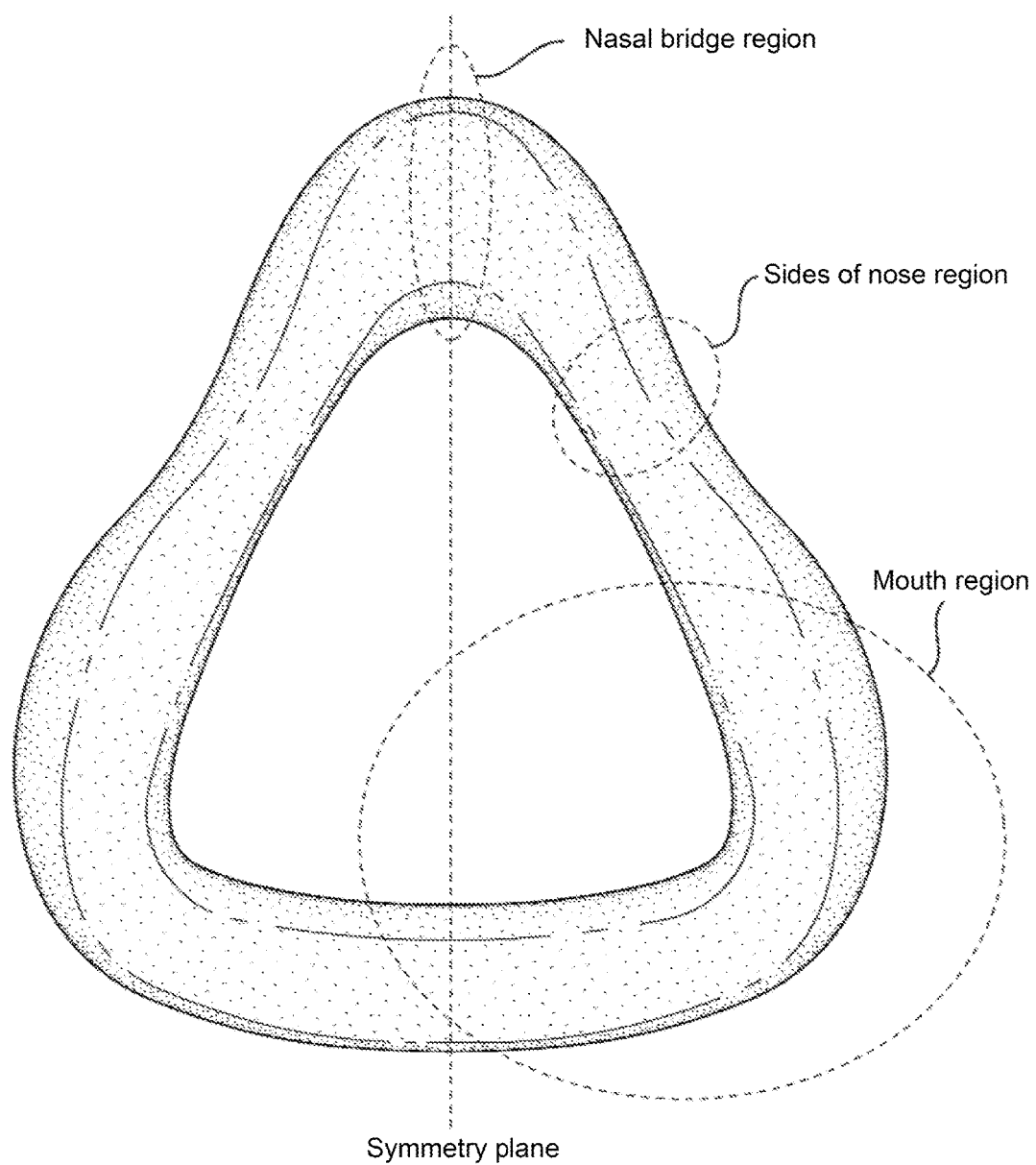
FIG. 7 shows regions of a clip component of the mask of FIG. 4.

Foam Details—FIG. 7

In this embodiment the foam has a varying cross section from the bridge of the nose to the bottom of the mouth, and is symmetric through the center plane. It should be noted the geometry of the foam is affected by, the anthropometric data used in the overall design of the soft clip and the specification of the foam material (ie hardness).

The varying cross section can be divided into three regions, nasal bridge, sides of nose and mouth, with a smooth transition between each of the regions. Each section is designed with a profile that is optimized for the specific are of the phase it seals with.

The cross section of the foam is designed to take into account of the following, and the geometry is design to address each of the areas.

Comfort

It was found with an increase in the amount of foam (both height and width) there is an increase in overall comfort. Depending on the specific cross section of the clip, the clip becomes noticeable and can be felt through the foam for heights <8 mm. (For the current embodiment, the range for the height of the foam is 8 mm-16 mm Similarly the comfort of the cushion was significantly impacted for width <12 mm. For the foam used in the prototype the width should be in the range of 12 mm to 30 mm, and the optimum being 15-20 mm.

Seal

It was found the seal is improved with an increase in width for the surface of the foam that is directly in contact with the patient.

Stability

It was found the stability of the seal is negatively impacted by an increase in the height of the foam, whilst being positively impacted by an increase in the width of the foam.

Encroachment

The main risk of encroachment is the potential for the cushion assembly to intrude/obstruct the user's eyes, one solution is to reduce the width of the foam in these areas. As the design was aiming at minimizing the overall size of the mask, attempts were made to minimize both the height and the width of the foam cushion.

Foam Cross Sections

Figure 8:
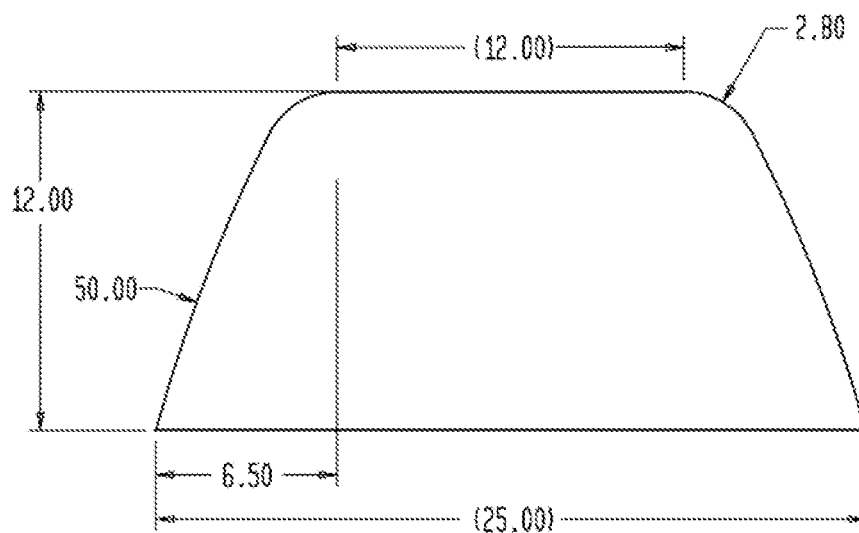

Nasal Bridge Region—FIG. 8

A trapezium shape was chose for its stability characteristics, with the top corners rounded for comfort. The width of 12 mm (with a range of 0-25 mm) for the surface contacting the user's nasal bridge is substantially higher than in other regions in order to increase the sealing surface in this region.

Figure 9:
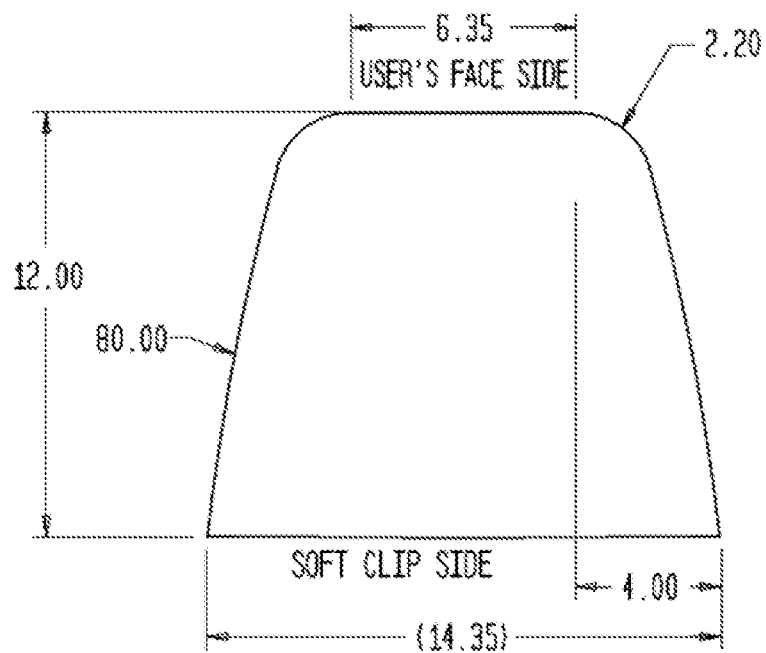

Side of Nose Region—FIG. 9

A trapezium shape was chose for its stability characteristics, with the top corners rounded for comfort. The width for the surface contacting the user's face has been reduced to 6.35 mm (with a range of (0-14 mm) in order to avoid the cushion intruding into the patient's eyes.

Mouth Region—FIG. 10

A trapezium shape was chose for its stability characteristics, with the top corners rounded for comfort. The length of 9 mm (with a range of 0-17 mm) for the surface contacting the user is a compromise between comfort/seal and overall mask size.

Other possible geometries include the following:

A cross section with a fully rounded top surface. This increases clearance between the user and the foam and improves overall stability.

A rectangular cross section, which is expected to perform similarly to the current embodiment, as the current embodiment for performance purposes is essentially a rectangular cross section with rounded corners. The rounded corner increases the overall comfort of the cushion as it removes the sharp corners.

It should be noted that a combination of geometries can be used in a single foam cushion (ie the foam could transition from a cross section with a flat top for comfort to a round top to increase clearance around specific areas).

The embodiment shown has a constant foam height of 12 mm, but the foam could also have a change in height along the foam to change the performance in individual sections of the cushion.

Possible Foam Cross Sections—FIG. 11

Material

The foam can be made with (but is not limited to) or a combination of the following: Polyethylene, Polyurethane, EVA Manufacture The current embodiment of the foam is produced via compression cutting, but it could be produced via or a combination of the following methods including, Die cutting
Thermoforming
Moulding
Grinding
Compression cutting The foam is compression cut to a flat profile as illustrated below. In this flat profile, the foam's shape is somewhat two dimensional, as its shape is mainly defined in two dimensions, but is planar in the third dimension. Once the foam is attached to the soft clip, it not only changes its two-dimensional shape, but also bends in the third plane (dimension) and becomes truly 3-dimensional. In this configuration, the foam is held to its contoured shape by the soft clip, as shown in FIG. 12.

Figure 12:
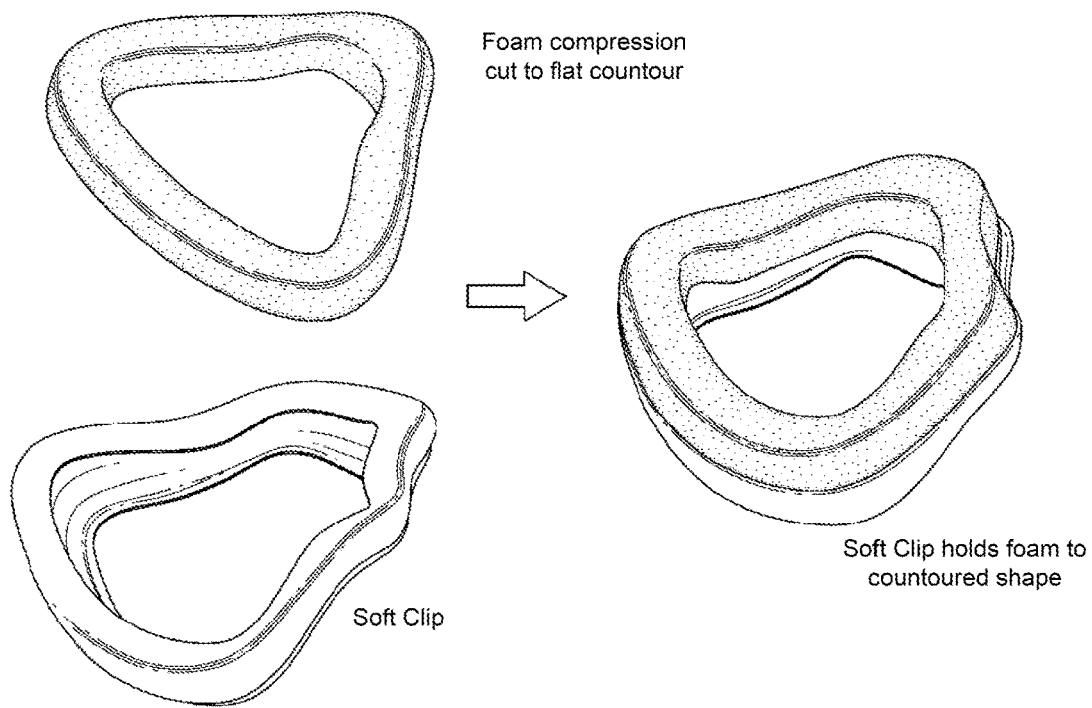
FIG. 12 illustrates foam cushion and clip components, as separate components, as well as in an assembled configuration.

Assembly Method—FIG. 12

The foam can be assembled onto the soft clip with

Figure 13:
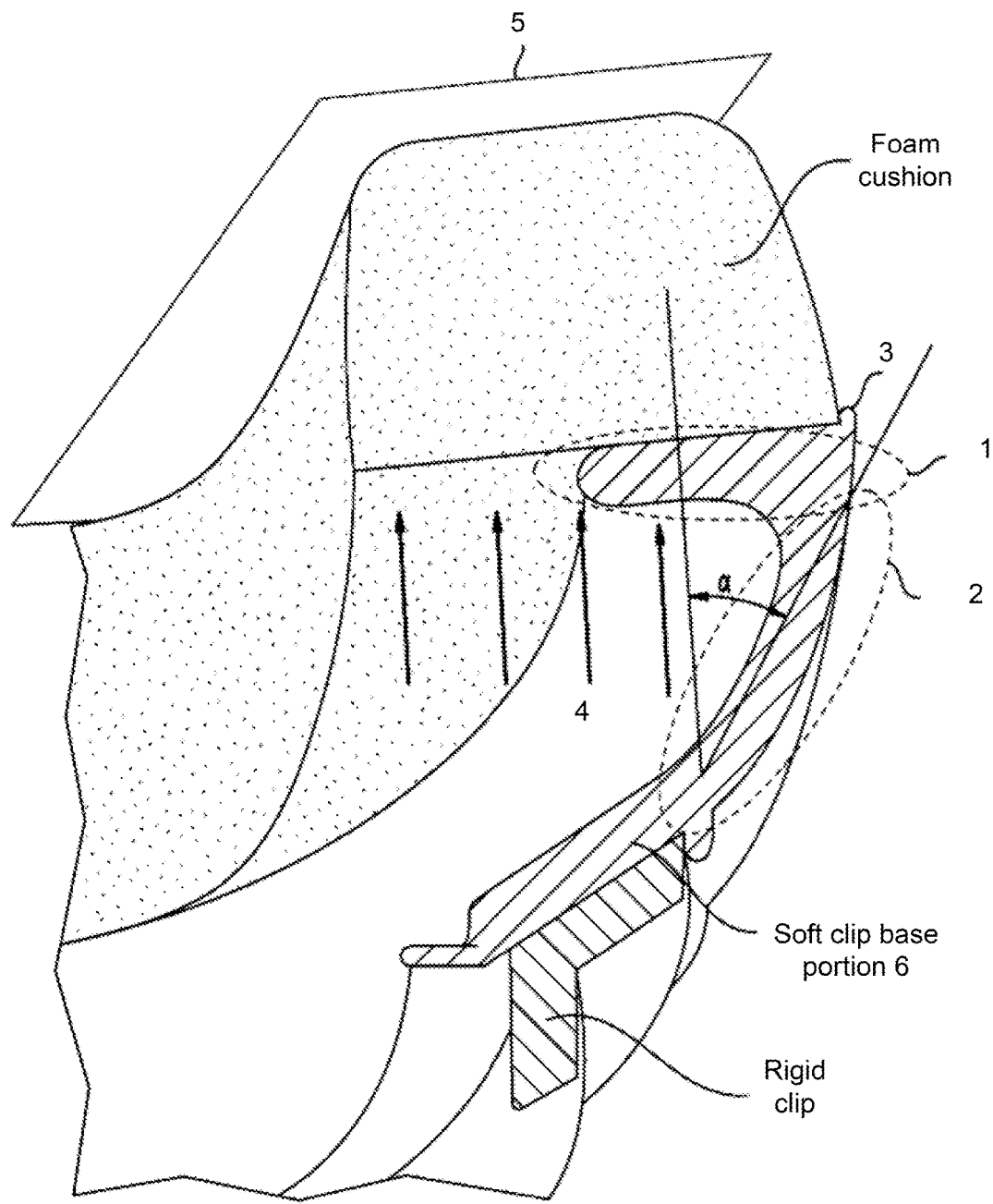
FIG. 13 is a cross sectional view of a cushion assembly with clip components and a foam cushion.
Figure 14:
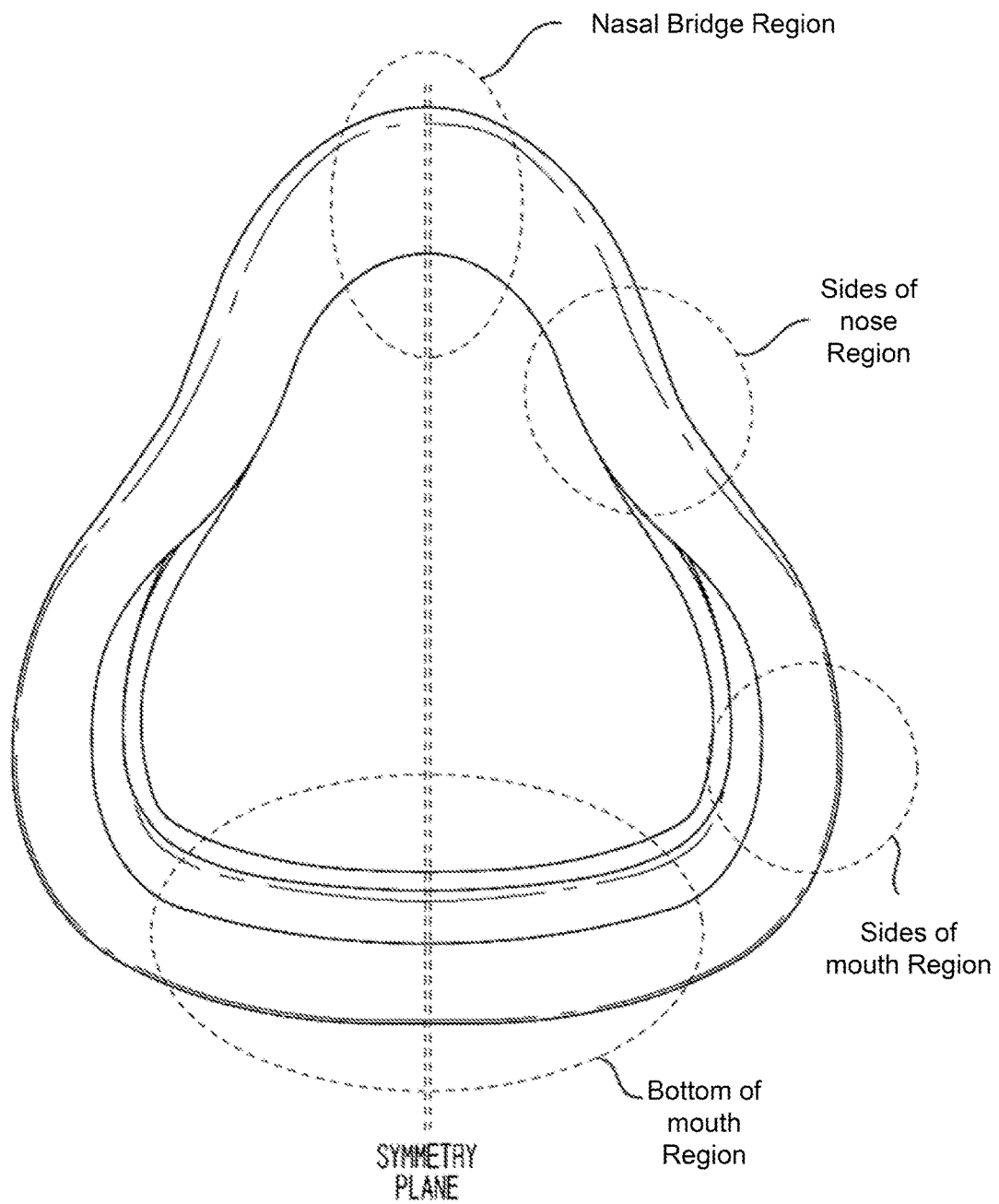
FIG. 14 shows various regions of a flexible clip component.
Figure 15:
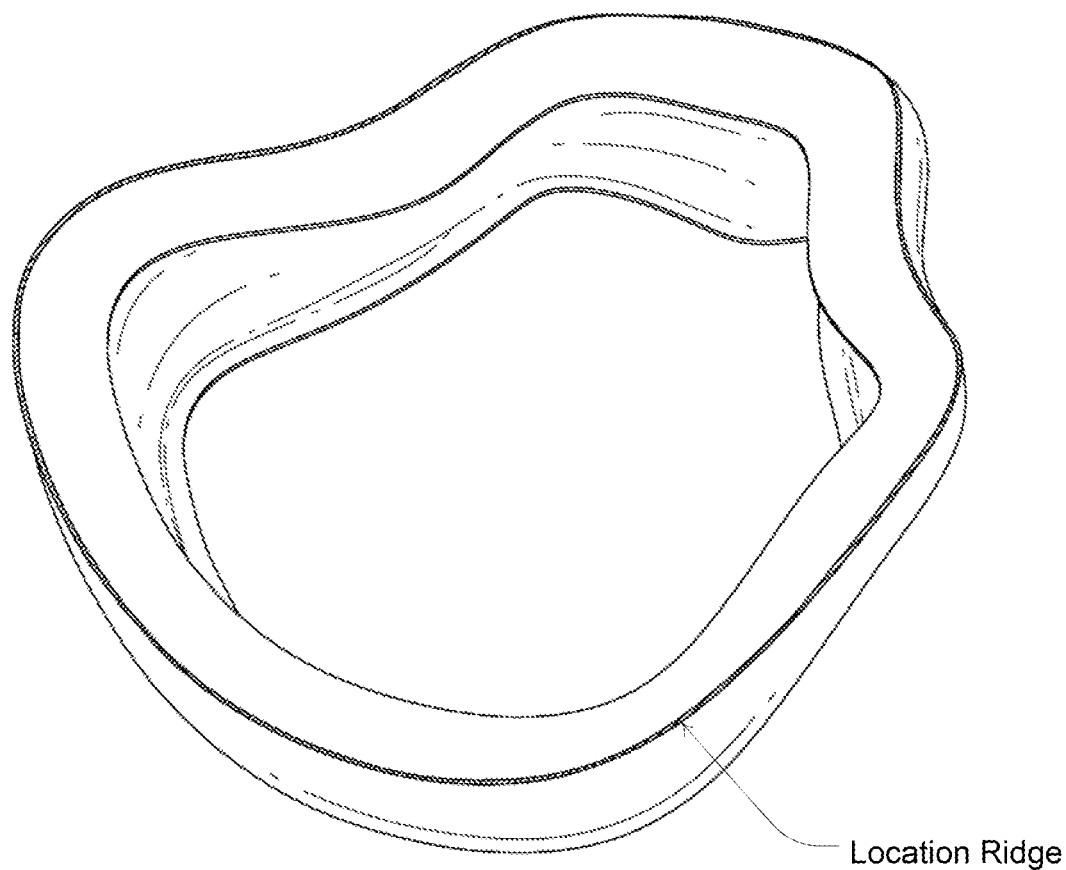
FIG. 15 shows the clip component of FIG. 14 with a foam location ridge.

Adhesive glue
Adhesive tape
Flame lamination
Moulding (moulding of foam onto the soft clip, or vice versa)
Welding
Mechanical connection between foam and soft clip
Sewing Soft Clip Details—FIG. 13 to FIG. 15

As can be seen from the clip cross-section illustrated in FIG. 13, the soft clip includes a cushion coupling portion 1, a support portion 2 and a base portion 6. The cushion coupling portion 1 provides a contact surface to which the cushion is attached. The supporting portion 2 is flexible and provides reaction support to the cushion when the headgear associated with the mask applies tension to the cushion. The base portion 6 attaches to the rigid clip or, in some embodiments, to the frame. More than one support portions 2, for example having different flexibility, can be included between the coupling portion 1 and the base portion 6.

The soft clip has a generally inwardly open (or concave) cross-section that varies in shape, but can generally be described as L or C, or even Z-shaped, with the opening being directed inwardly towards the center of the mask. The open or concave cross-section allows the pressure inside the mask chamber to be applied to the rear side of the cushion in a way that enhances the sealing. The support portion 2 is generally perpendicular to the sealing plane 5 (for example—see the C-shaped cross section and its respective support portion 2 in FIG. 21). The flexibility, the shape and the dimensions (in particular the thickness and the height) of the support portion of the clip can be chosen so that the soft clip can act as a cantilever spring. This cantilever spring allows the foam cushion to further conform to the face and compress towards it once alignment has been achieved, improving cushion compliance to the face.

A minimum height of about 5 mm is required in the soft clip to allow for sufficient movement during usage, so the user does not "bottom out" on the soft clip. ("bottoming out" occurs when the soft clip has reach its deflection limits and there is a sharp rise in the tension force acting on the user's face and experienced by the user) The height can very substantially within a range of about 5 mm to 30 mm, depending on the area of the face covered by the clip.

As discussed above, the two main active portions of the clip are shown in FIG. 13:

The flexible peripheral lip 1 that connects to the foam that forms an effective cantilever over-hang portion The middle portion 2 of the "C" or "L" section (the section between the over-hang portion supporting the foam, and the rigid clip). This section acts as springs and provides a sealing reaction force (As the section deforms it creates a reaction force which tries to return the clip to its original shape). This is why it is also referred to as a support portion 2.

Whilst support portion 2 of the clip is generally perpendicular to the sealing plane 5, as it can be seen in FIG. 13, in some embodiments there may be an angle α between the direction of support portion 2 and the perpendicular to the sealing plane 5. The introduction of such an angle α offers a particular compromise between support and flexibility. Thus, by varying the dimensions (mainly the thickness and the height), the rigidity and the shape (the angle α and/or the relative length of the arms of the L, C or Z shape) along the perimeter of the clip, different levels of support and flexibility are provided in the different sections of the mask. For example where higher softness and lower support is needed, such as in the sensitive area of the nasal bridge, the clip may use one, or combination of two or more of the following features: higher support portion 2, a thinner support portion 2 or an increased angle α. For example, angles between 20° and 50°, and more specifically between 30° and 40°, may be suitable for such applications. Variations in the overall physical structure of the soft clip, such as changing the overall shape of the clip (i.e. from C to L) or changing the relative lengths of various sections of the clip (i.e changing the relative length of cushion coupling portion 1 or support portion 2) can also be used in order to achieve similar result.

As shown in FIG. 13, the overall clip and the flexible peripheral lip that supports the foam cushion are so designed that pressure 4 within the chamber acts on the rear surface (the surface directed away from the user's skin) of the soft clip section and cushion. Thus, when applied, the pressure pushes the foam cushion towards the patient's face, thereby reinforcing the seal created by the cushion. As pressure increases, so does the force creating the seal. Support portion 2 of the clip may be chosen to have dimensions (height and thickness) and material properties (flexibility) that would allow the air pressure to create an air spring effect. The shape, the dimensions and the material characteristics of the support portion 2 may be selected so as to enable the clip to at least partially expand, in a balloon-like manner, under the effect of pressure applied to the mask when the cushion assembly is in use. Such an arrangement will further contribute to the overall compliance of the cushion assembly.

In this embodiment, as shown in FIG. 14, the soft clip has a varying cross section from the bridge of the nose to the bottom of the mouth, and is symmetric through the center plane. It should be noted the geometry of the soft clip will largely be affected by the overall design of the foam and the specification of the soft-clip material. For this particular embodiment the thickness of the soft clip in both Lip 1 and support portion 2 varies between 1 mm to 2 mm.

A location ridge, shown as region 3 in FIG. 13 and highlighted in FIG. 15 is included on the surface of the soft clip that contacts the foam (region 1), this aids alignment if the manufacturing process necessitate the alignment of the foam to the soft clip. The location ridge is designed to be small and does not come into contact with the user's face, in this embodiment it is 0.5 mm in height and width with a full round on the top. (With a range of 0.2-2 mm).

The different cross section in the various portions of the clip is intended to impart different properties to the associated sections of the mask and allow efficient sealing with the respective regions of the user's face, as described in detail below.

Nasal Bridge—FIG. 16

The cross section in this region is "C" shaped and is designed to allow the foam to move substantially perpendicularly to the user's face to accommodate a wide range of nasal bridge depth. It forms the softest part of the soft-clip and has a thickness (support portion 2) of 1 mm (with a range of 0.25-1.5 mm). The movement is generated by the angle between the inner face (in this case 45°) (with a range 0° to 90°) and the overall size of the "C" section.

The surface that attaches to the foam (lip 1) is the largest in this area (15 mm) (range of 10-25 mm), this is done to reduce the likelihood of the seal from blowing out on the sides of the nose, as it restricts the outward movement of the soft clip in the this region.

It's the combination of these values which define the overall sealing and comfort quality.

Sides of Nose—FIG. 17

The cross section of the clip in this portion of the mask is still "C" shaped and is designed to allow the foam to pivot and match the facial geometry to the sides of the user's nose. This allows the foam contact surface to be parallel with the user's nose. The soft clip (support portion 2) has a thickness in this region of 1 mm. (with a range of 0.25-1.5 mm).

The height of 12 mm (with a range of 8 mm-20 mm) gives the range of movement necessary to conform to the user's nose.

Figure 18:
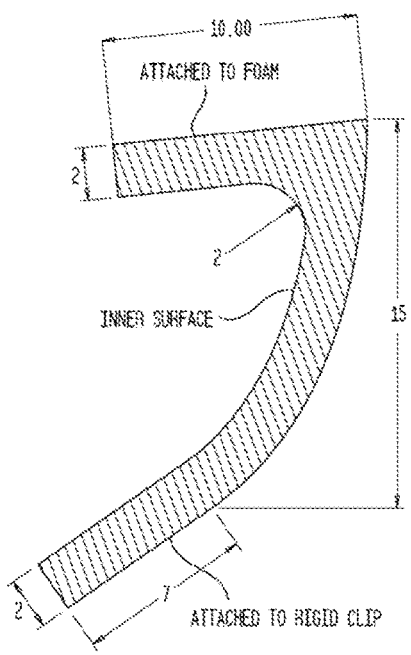

Sides of Mouth—FIG. 18

The clip cross section on both sides of the mouth is "L" shaped and is designed to be the most rigid, effectively forming an anchor point around the sides of the mouth. This design is used as these regions of the face are deemed to be the least pressure sensitive. Furthermore the cross section allows the foam to be pivoted into the user's face to allow for varying facial profiles. The soft clip and more particularly its support portion 2, has a thickness of 2 mm (with a range of 1.5 mm to 3 mm) to provide the increase in stiffness.

It should be noted a "C" shaped designed could be used in this area, but would result in an increase in overall mask footprint.

Figure 19:
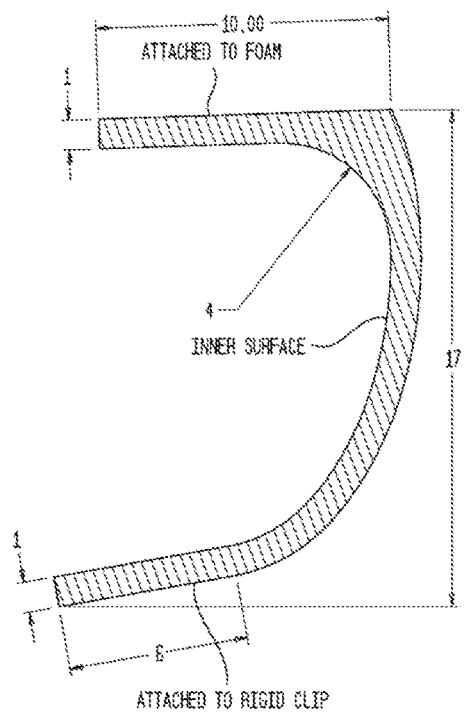

Bottom of Mouth—FIG. 19

The clip cross section here is "L" shaped and is designed to allow for the soft clip to roll. This allows the foam to move upwards and downwards relative to the face (left and right with respect to the image below) and maintain a parallel top sealing surface with respect to the user's face. This feature allows for movement of the user's jaw without loss in seal (ie jaw drop during usage). The soft clip has a thickness in this region of 1 mm (with a range of 0.25-1.5 mm). The rolling action is possible with inner surface being all rounded, this is further aided by having a larger radius (in this case 4 mm, with a range of 2 to 10 mm) which prevents the surface attached to the foam (lip 1) from folding inwards. The soft clip has a height of 17 mm (with a range of 15 to 25 mm) in this region and is required for sufficient movement of the foam cushion.

It should be noted a "C" shaped designed could be used in this area, but would result in an increase in overall mask footprint.

In the current embodiment a lip seal is used between the soft clip and the mask frame to ensure a seal is maintained between the two components. The lip seal is part of the soft clip.

Figure 20:
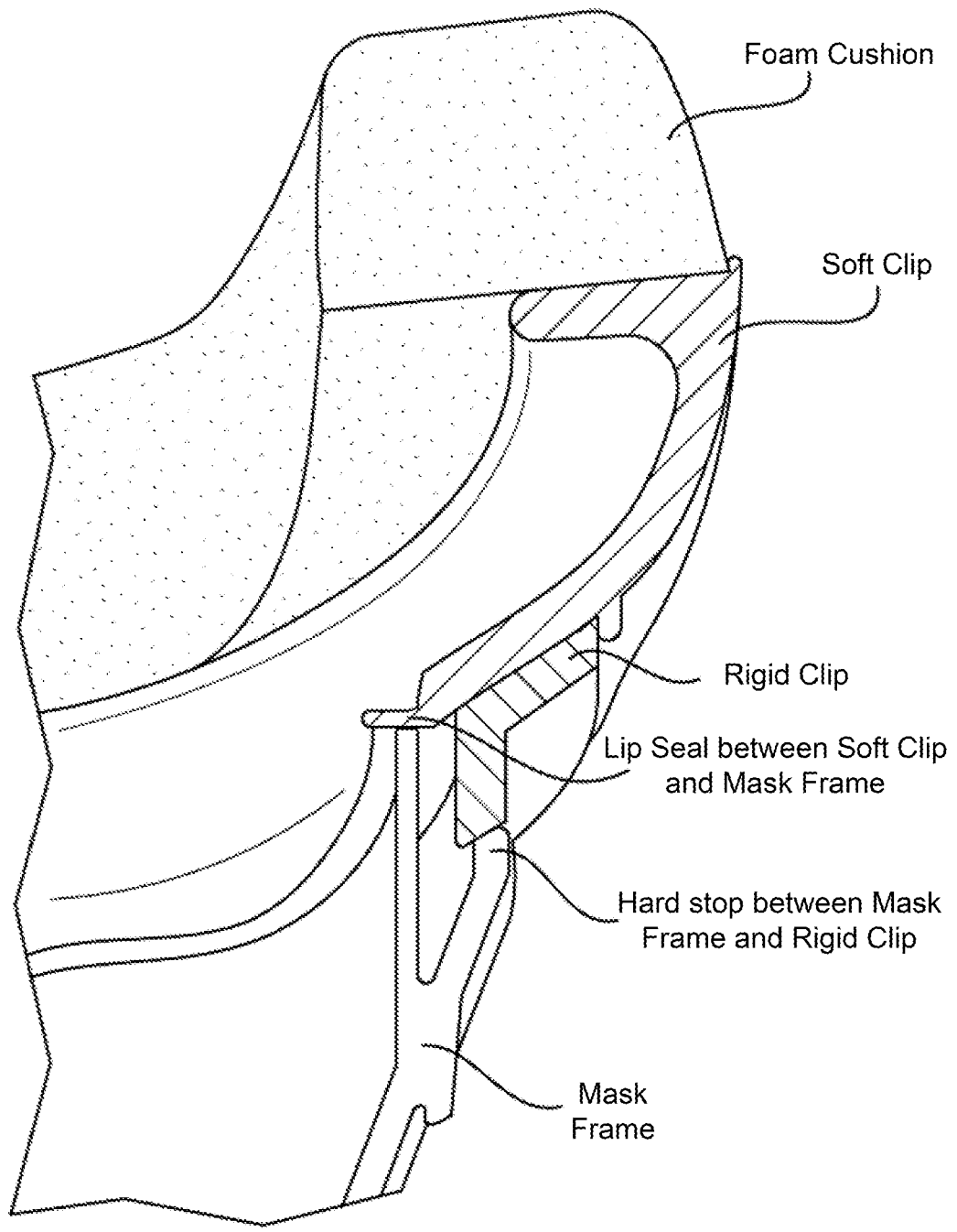
FIGS. 20 and 21 are cross sectional views of example cushion assemblies coupled with a mask frame.

The interface between the rigid clip and the Mask frame is shown in FIG. 20 and it acts as the hard stop, which prevents the cushion assembly from being pushed too far into the mask frame. An incorrectly assembled cushion could lead to leaks through the lip seal, the mask frame protruding too far and contacting the patient, move the headgear attachments on the mask frame too far and causing contact with the patient.

The performance characteristics (how it behaves under load, ie increase/decrease in sealing force) can be altered in the individual sections of the soft clip by modifying the following.

Material properties
Soft Clip thickness
Overall soft clip height and width
Soft Clip geometry
Materials The soft clip is made from an elastic material that will deform under load. This includes but is not limited to, silicone, TPE, TPU and natural rubbers.

TPE material is preferred as it has a higher potential to be adhered to/moulded to the foam.

Manufacture

The manufacturing process of the soft clip is injection moulding, where it can be moulded in the following manner:
As a separate component
Overmoulded onto the hard clip
Moulded to both the foam and the hard clip.

Depending on the manufacturing process, if the soft clip is manufactured as a separate component, it could be assembled to the hard clip via:
Adhesive glue
Adhesive tape
Flame lamination
Ultrasonic welding
Hard Clip Details—FIG. 21 and FIG. 22

Figure 21:
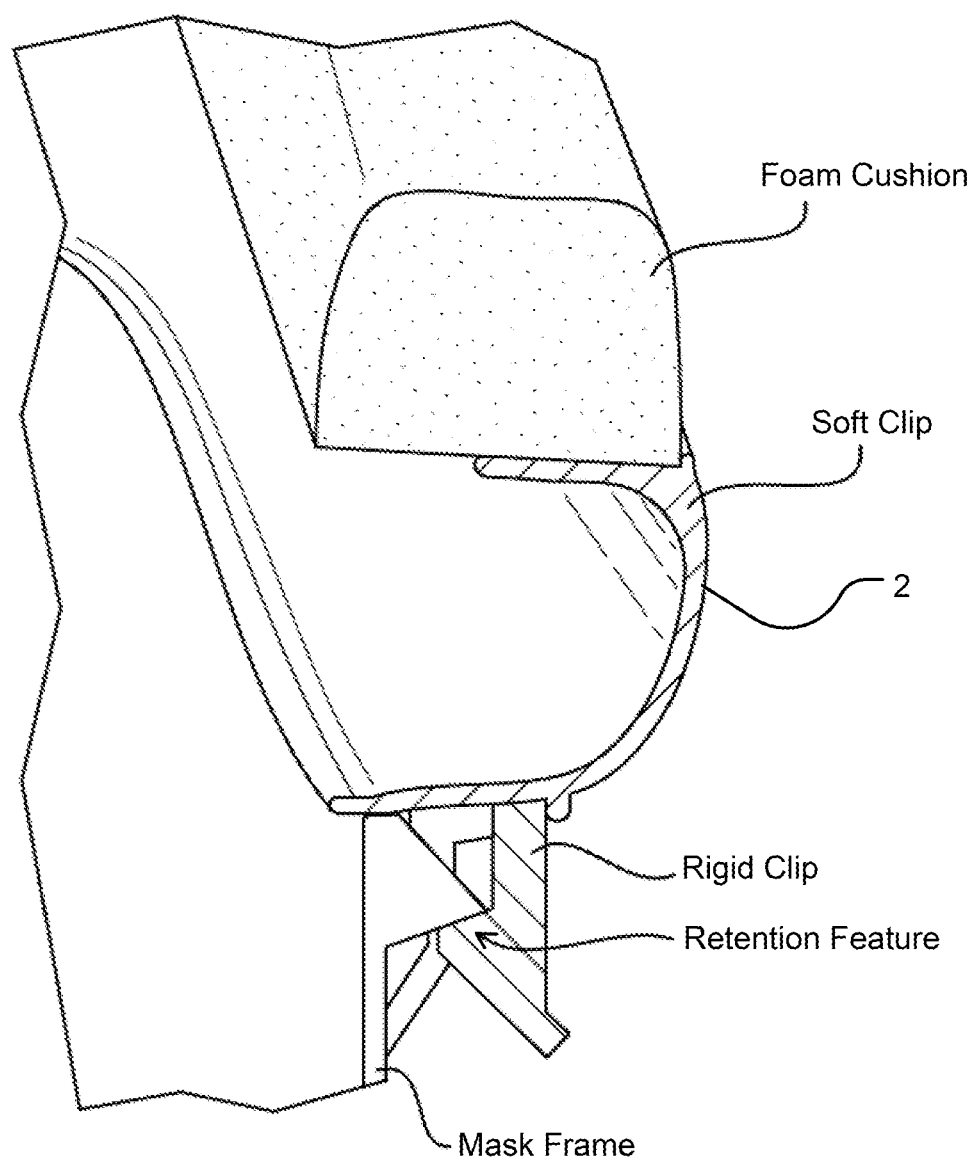
Figure 22:
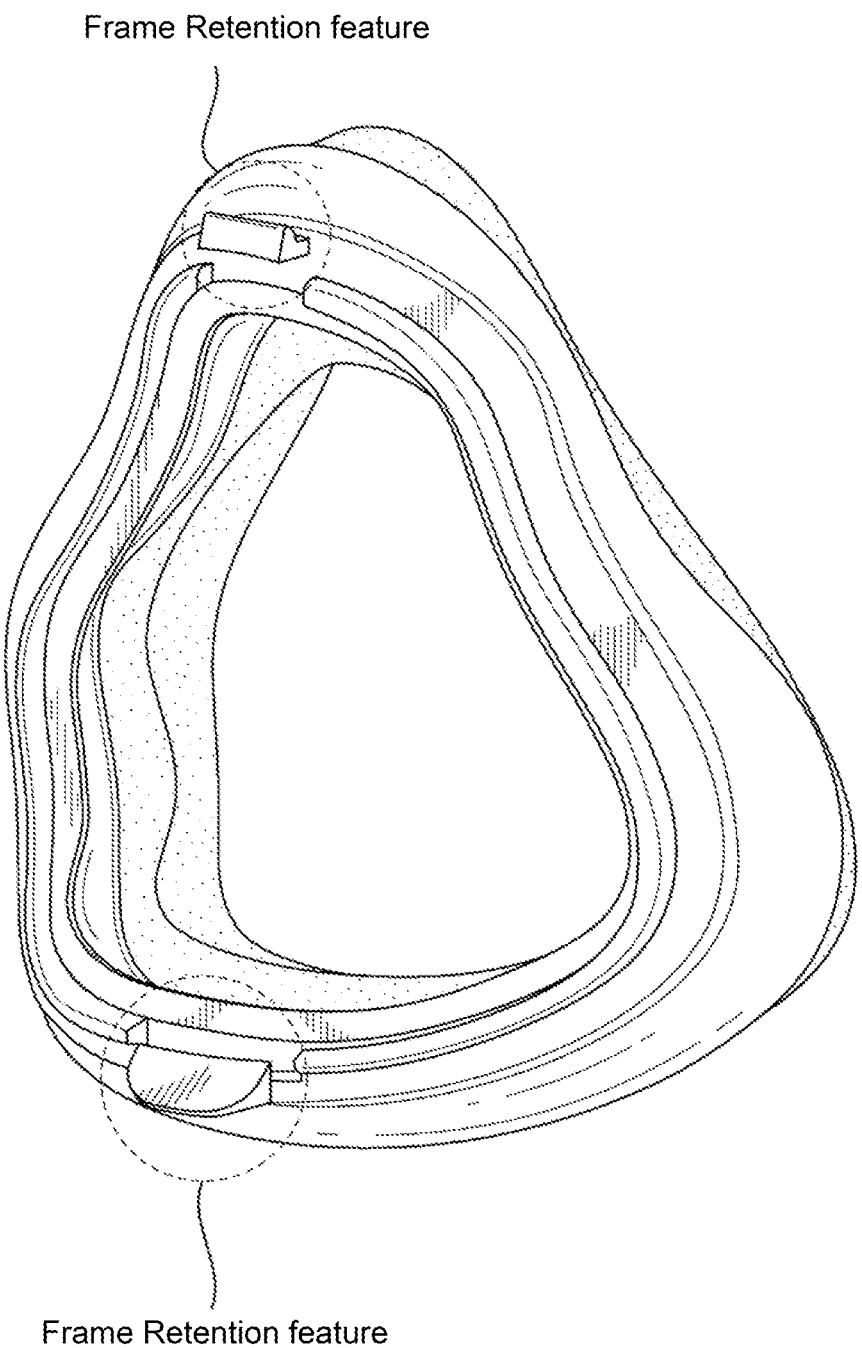
FIG. 22 illustrates several frame retention features for coupling a foam mask cushion assembly with a mask frame.

The main purposes of the hard clip are:
1. Allows for easy disassembly of the cushion assembly from the mask frame
    This is required for ease of cleaning of the mask frame and for the replacement of the cushion assembly. One retention mechanism between the cushion assembly and the mask frame is shown below. One retention mechanism shown in FIGS. 21 and 22 represents a plurality of retaining clips that clip to respective surfaces of the frame and abbutingly support the rigid clip, as well as the soft clip attached to the rigid clip, to the frame. Alternative assemblies are also possible.
2. The hard clip allows for a hard interface between the soft clip/foam assembly and the mask frame. Whilst the use of hard clip may increase usability, it is not essential for the operation of the mask. Alternate attachment mechanisms can be used to attach the cushion assembly to the mask frame. Similarly, it is envisaged that a mask assembly may be designed that may not necessarily include the soft clip.
    Alternative assembly mechanisms between the foam cushion and the mask frame, some of which do not include rigid or even soft clip, include:
        Tongue and groove geometry between the soft clip and the Mask Frame
        The soft clip stretches around the Mask Frame
        The soft clip contains an interference fit similar to air-tight food containers.
        Tongue and slot interface between the soft clip and the Mask Frame with secondary lip seal or gasket present
        Cushion assembly permanently attached to the Mask Frame
        Adhesive tape between the cushion assembly and the Mask Frame
3. The hard clip provides structural integrity to the cushion assembly
    Due to the soft nature of the soft clip and foam cushion, the hard clip also provides a rigid structural element to the cushion assembly, which allows it to hold its shape whilst being disassembled from the mask frame.

Materials

The hard clip can be made of a rigid thermoplastic material, such as but is not limited to ABS, Nylon, Polycarbonate.

Manufacture

The preferred manufacturing process is injection moulding.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A foam cushion assembly for a patient interface, the foam cushion assembly being adapted to couple with a patient interface frame, the cushion assembly comprising a nose seal portion and a mouth seal portion, wherein the cushion assembly comprises:
    a foam cushion arranged to form a portion of a plenum chamber for sealing about the nose and mouth, the foam cushion having a facial contact surface; and
    a cushion support clip comprising a mounting portion with a ratio of width to thickness of the mounting portion, the ratio being greater than three, the cushion support clip having an inwardly concave cross section and being flexible in its concave portion to provide, in use, one or more of (a) deflection of the foam cushion relative to the frame; (b) an air spring to the foam cushion, the air spring responsive to pressurized gas in the cushion assembly; and (c) a cantilever spring for the foam cushion.

2. The foam cushion assembly of claim 1, wherein the cushion support clip is arranged to enable an air spring effect of pressure in the patient interface, when in use.

3. The foam cushion assembly of claim 1, wherein shape, dimensions and material characteristics of the cushion support clip are selected so as to enable the clip to at least partially expand in a balloon-like manner, under effect of pressure applied to the patient interface, when in use.

4. The foam cushion assembly of claim 1, the cushion assembly further comprising a second support clip configured to couple with the cushion support clip and the frame.

5. The foam cushion assembly of claim 4, wherein the second support clip is more rigid than the cushion support clip and the cushion support clip is more rigid than the foam cushion.

6. The foam cushion assembly of claim 4, wherein the foam cushion, the cushion support clip and the second support clip are integrally connected.

7. The foam cushion assembly of claim 1, wherein the foam cushion and the cushion support clip are integrally connected.

8. The foam cushion assembly of claim 1 wherein the cushion support clip forms an inwardly overhanging peripheral lip for mounting the foam cushion.

9. The foam cushion assembly of claim 1 wherein the cushion support clip is configured to provide a roll response toward the plenum chamber when in use.

10. The foam cushion assembly of claim 1 wherein the foam cushion is arranged to form a sealing surface at a facial periphery surrounding the nose and mouth in use, and wherein the cushion support clip is arranged with a surface to attach the foam cushion about said facial periphery of the plenum chamber, the cushion support clip being inwardly concave along said facial periphery including a bottom of mouth region.

11. The foam cushion assembly of claim 1 wherein the concave portion varies in cross sectional shape along a perimeter of the plenum chamber from a C shape to an L shape.

12. The foam cushion assembly of claim 1 wherein the cushion support clip comprises side of nose regions along the perimeter, each with an inwardly concave form having a C cross sectional shape.

13. The foam cushion assembly of claim 1 wherein the cushion support clip comprises side of mouth regions along the perimeter, each with an inwardly concave form having an L cross sectional shape.

14. The foam cushion assembly of claim 1 wherein the cushion support clip comprises a bottom of mouth region along the perimeter with an inwardly concave form having an L cross sectional shape.

15. The foam cushion assembly of claim 1 wherein the cushion support clip comprises:
- side of nose regions along the perimeter, each with an inwardly concave form having a C cross sectional shape; and
- side of mouth regions along the perimeter, each with an inwardly concave form having an L cross sectional shape.

16. The foam cushion assembly of claim 1 wherein the cushion support clip comprises:
- side of nose regions along the perimeter, each with an inwardly concave form having a C cross sectional shape;
- side of mouth regions along the perimeter, each with an inwardly concave form having an L cross sectional shape; and
- a bottom of mouth region along the perimeter with an inwardly concave form having an L cross sectional shape.

17. The foam cushion assembly of claim 1 wherein the cushion support clip is formed of silicone.

18. The foam cushion assembly of claim 1 wherein the cushion support clip is formed of natural rubber.

19. The foam cushion assembly of claim 1 wherein the cushion support clip is formed of a thermoplastic elastomer.

20. The foam cushion assembly of claim 1 wherein the cushion support clip is formed of a thermoplastic polyurethane.

21. The foam cushion assembly of claim 1 wherein the cushion support clip has a height in a range of 5 mm to 30 mm.

22. The foam cushion assembly of claim 21 wherein the cushion support clip has a height in a range of 8 mm to 20 mm in sides of nose regions.

23. The foam cushion assembly of claim 21 wherein the cushion support clip has a height in a range of 15 mm to 25 mm in a bottom of mouth region.

24. The foam cushion assembly of claim 1 wherein a support portion of the cushion support clip forms an angle with a perpendicular to a sealing plane of the foam cushion, the angle being in a range of 20 degrees to 50 degrees.

25. The foam cushion assembly of claim 24 the angle is in a range of 30 degrees to 40 degrees.

26. The foam cushion assembly of claim 1 wherein the concave portion provides deflection of the foam cushion relative to the frame in use.

27. The foam cushion assembly of claim 1 wherein the concave portion provides an air spring to the foam cushion, the air spring responsive to the pressurized gas in the cushion assembly in use.

28. The foam cushion assembly of claim 1 wherein the concave portion provides a cantilever spring for the foam cushion in use.

29. The foam cushion assembly of claim 1 wherein the concave portion provides, in use, (a) deflection of the foam cushion relative to the frame; b) an air spring to the foam cushion, the air spring responsive to the pressurized gas in the cushion assembly; and (c) a cantilever spring for the foam cushion.

30. The foam cushion assembly of claim 1 wherein the foam cushion is attached to the mounting portion to form a contact surface joining the foam cushion and the mounting portion, wherein the contact surface has a cross-sectional width equal to the width of the ratio.

31. The foam cushion assembly of claim 30 wherein the mounting portion has the thickness of the ratio along the contact surface.

32. The foam cushion assembly of claim 1 wherein the width of the ratio is in a range of 10 to 25 mm.

33. The foam cushion assembly of claim 32 wherein the thickness of the ratio is in a range from 0.25 to 3 mm.

34. The foam cushion assembly of claim 1 wherein the ratio is in a range of 3 to 100.

35. The foam cushion assembly of claim 34 wherein the ratio is about 15 in a nasal bridge region.

36. The foam cushion assembly of claim 35 wherein the width of the ratio is about 15 mm and the thickness of the ratio is about 1 mm.

37. The foam cushion assembly of claim 34 wherein the ratio is in a range of 6.7 to 40 in a side of nose region.

38. The foam cushion assembly of claim 37 wherein the width of the ratio is about 10 mm and the thickness of the ratio is about 1 mm.

39. The foam cushion assembly of claim 34 wherein the ratio is in a range of 3.3 to 6.7 in a side of mouth region.

40. The foam cushion assembly of claim 39 wherein the width of the ratio is about 10 mm and the thickness of the ratio is about 2 mm.

41. The foam cushion assembly of claim 34 wherein the ratio is in a range of 6.7 to 40 in a bottom of mouth region.

42. The foam cushion assembly of claim 41 wherein the width of the ratio is about 10 mm and the thickness of the ratio is about 1 mm.

43. A patient interface apparatus for a respiratory treatment comprising:
- a frame adapted to couple with a respiratory treatment apparatus so as to permit communication of a pressurized gas to a respiratory system of a patient from the respiratory treatment apparatus; and
- a cushion assembly adapted to couple with the frame, the cushion assembly comprising a nose seal portion and a mouth seal portion, wherein the cushion assembly comprises:

a foam cushion arranged to form a portion of a plenum chamber for sealing about the nose and mouth, the foam cushion having a facial contact surface; and a cushion support clip comprising a mounting portion with a ratio of width to thickness of the mounting portion, the ratio being greater than three, the cushion support clip having an inwardly concave cross section and being flexible in its concave portion to provide, in use, one or more of (a) deflection of the foam cushion relative to the frame; (b) an air spring to the foam cushion, the air spring responsive to the pressurized gas in the cushion assembly; and (c) a cantilever spring for the foam cushion.

44. The patient interface apparatus of claim 43, wherein the cushion support clip is arranged to enable an air spring effect of the pressure in the patient interface, when in use.

45. The patient interface apparatus of claim 43, the cushion assembly further comprising a second support clip configured to couple with the cushion support clip and the frame.

46. The patient interface apparatus of claim 45, wherein the foam cushion, the cushion support clip and the second support clip are integrally connected.

47. The patient interface apparatus of claim 43, wherein the foam cushion and the cushion support clip are integrally connected.

48. The patient interface apparatus of claim 43 wherein the cushion support clip forms an inwardly overhanging peripheral lip for mounting the foam cushion.

49. The patient interface apparatus of claim 43 wherein the cushion support clip is configured to provide a roll response toward the plenum chamber when in use.

50. The patient interface apparatus of claim 43 wherein the foam cushion is arranged to form a sealing surface at a facial periphery surrounding the nose and mouth in use, and wherein the cushion support clip is arranged with a surface to attach the foam cushion about said facial periphery of the plenum chamber, the cushion support clip being inwardly concave along said facial periphery including a bottom of mouth region.

51. The patient interface apparatus of claim 43 wherein the foam cushion is attached to the mounting portion to form a contact surface joining the foam cushion and the mounting portion, wherein the contact surface has a cross-sectional width equal to the width of the ratio.

52. The patient interface apparatus of claim 51 wherein the mounting portion has the thickness of the ratio along the contact surface.

53. The patient interface apparatus of claim 43 wherein the width of the ratio is in a range of 10 to 25 mm.

54. The patient interface apparatus of claim 53 wherein the thickness of the ratio is in a range from 0.25 to 3 mm.

55. The patient interface apparatus of claim 43 wherein the ratio is in a range of 3 to 100.

56. The patient interface apparatus of claim 55 wherein the ratio is about 15 in a nasal bridge region.

57. The patient interface apparatus of claim 56 wherein the width of the ratio is about 15 mm and the thickness of the ratio is about 1 mm.

58. The patient interface apparatus of claim 55 wherein the ratio is in a range of 6.7 to 40 in a side of nose region.

59. The patient interface apparatus of claim 58 wherein the width of the ratio is about 10 mm and the thickness of the ratio is about 1 mm.

60. The patient interface apparatus of claim 55 wherein the ratio is in a range of 3.3 to 6.7 in a side of mouth region.

61. The patient interface apparatus of claim 60 wherein the width of the ratio is about 10 mm and the thickness of the ratio is about 2 mm.

62. The patient interface apparatus of claim 55 wherein the ratio is in a range of 6.7 to 40 in a bottom of mouth region.

63. The patient interface apparatus of claim 62 wherein the width of the ratio is about 10 mm and the thickness of the ratio is about 1 mm.

* * * * *